(12) United States Patent
Petit et al.

(10) Patent No.: US 10,448,880 B2
(45) Date of Patent: Oct. 22, 2019

(54) METHOD FOR MEASURING FLUSHING AND USE FOR ASSESSING TREATMENTS

(71) Applicant: GALDERMA RESEARCH & DEVELOPMENT, Biot (FR)

(72) Inventors: Laurent Petit, F-Peymeinade (FR); Anne-Sophie Dugaret, Juan les Pins (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 644 days.

(21) Appl. No.: 14/780,278

(22) PCT Filed: Mar. 28, 2014

(86) PCT No.: PCT/EP2014/056322
§ 371 (c)(1),
(2) Date: Sep. 25, 2015

(87) PCT Pub. No.: WO2014/154877
PCT Pub. Date: Oct. 2, 2014

(65) Prior Publication Data
US 2016/0051181 A1 Feb. 25, 2016

(30) Foreign Application Priority Data
Mar. 29, 2013 (FR) .................................. 13 52854

(51) Int. Cl.
*A61B 5/00* (2006.01)
*A61B 5/026* (2006.01)
*A61B 5/103* (2006.01)

(52) U.S. Cl.
CPC ............ *A61B 5/445* (2013.01); *A61B 5/0261* (2013.01); *A61B 5/1032* (2013.01); *A61B 5/4848* (2013.01); *A61B 5/7225* (2013.01); *A61B 5/6814* (2013.01)

(58) Field of Classification Search
CPC ............................... A61B 5/441; A61B 5/445
See application file for complete search history.

(56) References Cited

U.S. PATENT DOCUMENTS

| | | |
|---|---|---|
| 2004/0181375 A1 | 9/2004 | Szu et al. |
| 2012/0078114 A1 | 3/2012 | Mersch et al. |
| 2015/0157271 A1* | 6/2015 | Zhang ................ A61B 5/7246 600/324 |

OTHER PUBLICATIONS

Laser Speckle Contrast Imaging of Cerebral Blood Flow. Andrew K. Dunn. p. 367-377. Annals of Biomedical Engineering, vol. 40, No. 2, Feb. 2012.*

(Continued)

*Primary Examiner* — Christian Jang
(74) *Attorney, Agent, or Firm* — Foley & Lardner LLP; Sunit Talapatra

(57) ABSTRACT

A method is described that makes it possible to measure flushing, particularly in the context of the study of rosacea, and to distinguish normal flushing from pathological flushing. Also described, is the use of said method to study the effect of drug candidates, particularly against rosacea. The method can include: a) subjecting the subject to a flushing inducing stimulus; b) measuring the inflow of blood in the face of the subject during a time period covering the flushing; and c) calculating entropy of the inflow of blood.

23 Claims, 5 Drawing Sheets

(56) References Cited

OTHER PUBLICATIONS

International Search Report and Written Opinion dated Aug. 21, 2014 corresponding to International Patent Application No. PCT/EP2014/056322, 11 pages.
English Translation of the International Search Report dated Aug. 21, 2014 corresponding to International Patent Application No. PCT/EP2014/056322, 3 pages.
Singer, Em., et al.,"Human Clinical Research and Therapeutics Abstracts 931 IL-31 is produced by the malignant T cell population in cutaneous T-cell lymphoma and its expression correlates with pruritus Development of a GMP facility for cell therapy of chronic non-n=healing wounds," Jan. 2013, Retrieved from the Internet: URL:http://www.nature.com/jid/journal/v133/nls/pdf/jid201302a.pdf [retrieved on Nov. 26, 2013], 982.
Wilkin, J.K., "Oral thermal-induced flushing in erythematotelangiectatic rosacea," Journal of Investigative Dermatology, vol. 76, Jan. 1981, pp. 15-18.
Weiss, S., et al., "The velocity of blood flow in the health and disease as measured by the effect of histamine on the minute vessels," American Heart Journal, vol. 4, No. 6, Aug. 1929, pp. 664-691.

* cited by examiner

FIGURE 6
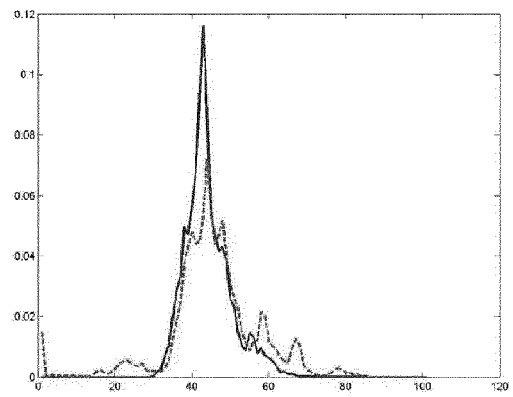
Fig. 7A         Fig. 7B
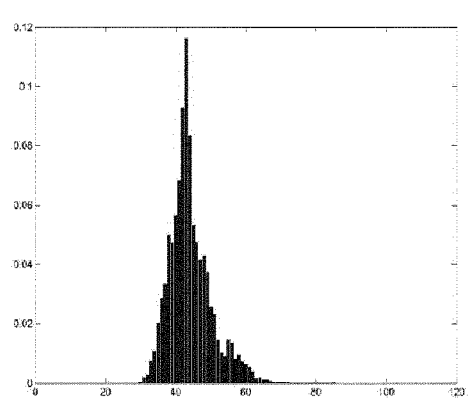 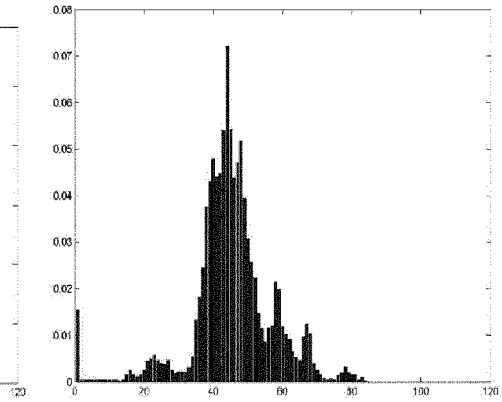
FIGURE 8
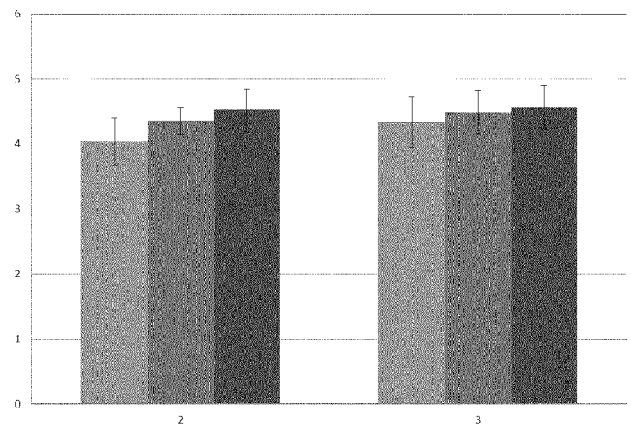

|  | Stimulus | Hot water | Tabasco |
|---|---|---|---|
| n per group | Based on AUC | 55 | 124 |
|  | Based on the entropy | 13 | 16 |

METHOD FOR MEASURING FLUSHING AND USE FOR ASSESSING TREATMENTS

CROSS-REFERENCE TO PRIOR APPLICATIONS

This application is a National Stage of PCT/EP2014/056322, filed Mar. 28, 2014, and designating the United States (published on Oct. 2, 2014, as WO 2014/154877 A1), which claims priority under 35 U.S.C. § 119 to French Patent Application No. 1352854, filed Mar. 29, 2013, each hereby expressly incorporated by reference in its entirety and each assigned to the assignee hereof.

FIELD OF THE INVENTION

The present invention relates to the field of medicine. In particular, it relates to a method for measuring flushing.

BACKGROUND OF THE INVENTION

Rosacea is a chronic and gradual common inflammatory dermatosis related to vascular disorders. It mainly affects the central portion of the face and is characterized by reddening of the face accompanied by hot flushes, facial erythema, papules, pustules, telangiectasias and sometimes ocular lesions called ocular rosacea. In extreme cases, especially in humans, hypertrophy is observed at the nasal level called rhinophyma. Rosacea evolves over several years with outbreaks worsened by various stimuli like temperature variations, alcohol, spices, solar exposure or emotions.

Rosacea is classified into four subtypes depending on various clinical characteristics (Wilkin J et al., JAAD, 2002, 46: 584-587).

Subtype 1: also called erythematotelangiectasic rosacea, mainly characterized by flushes and a persisting central facial erythema. The presence of telangiectasias is common, but not essential to the diagnostic of this subtype. A central facial oedema, burning and stinging sensations and roughness or desquamation are also sometimes observed. The patients have erythrosis outbreaks due to sudden dilation of the arterioles of the face which then assume a congestive, red aspect. These outbreaks are caused by emotions, meals, temperature variations and are designated by the term of flushes.

Subtype 2: Also called papulopustular rosacea, which is characterized by an inflammatory stage with occurrence of inflammatory papules and pustules but without attaining the sebaceous follicle and therefore with absence of cysts and comedos. Papulopustular rosacea is characterized by persistent central facial erythema and by transient papules and/or pustules distributed at the centre of the face. However, the papules and pustules may also affect peri-orificial regions (i.e. peribuccal, perinasal or periocular areas). The papulopustular subtype recalls ordinary acne, but the comedos are absent. Rosacea and acne may coexist and, in addition to the papules and pustules suggesting rosacea, the concerned patients will also possibly have comedos. Patients affected by papulopustular rosacea will sometimes complain of burning and stinging sensations.

Subtype 3: Called Phymatous Rosacea (Rhinophyma)

Phymatous rosacea shows signs of thickening of the skin, nodules with an irregular surface and swelling. Rhinophyma is the most common presentation but phymatous rosacea may affect other territories, including the chin, the forehead, the cheeks and the ears. In patients affected by this subtype, the presence of enlarged and prominent follicular apertures is sometimes reported in the affected region, as well as telangiectasias. This belated phase essentially affects men. The patients have a red voluminous nose, covered with bumps with sebaceous hyperplasia and fiber reorganization of the conjunctive tissue.

Subtype 4: Called ocular rosacea (or ophthalmic rosacea). Ocular rosacea is often poorly diagnosed or underestimated as a cause of conjunctival inflammation. The diagnosis of ocular rosacea should be contemplated when a patient has one or several of the following signs and ocular symptoms: watery or blood-injected aspect (interpalpebral conjunctival hyperemia), foreign body, burning or stinging sensation, dryness, itching, photosensitivity, blurred vision, telangiectasias of the conjunctiva and of the edge of the eyelid or erythema of the eyelid and periocular erythema. Blepharitis, conjunctivitis and irregularity of the edges of the eyelid are other possibly detected signs. A chalazion or a chronic staphylococcus infection, apparent as a sty, and the cause of which is a dysfunction of meibomian glands, is a frequent sign of ocular affection related to rosacea. Certain patients will complain of decreased visual acuity, which is due to corneal complications (punctated keratitis, corneal infiltrates/ulcerations of the cornea or marginal keratitis).

Flushing histories are common in patients affected with erythematotelangiectasic rosacea (subtype 1) and sometimes also in those affected with papulopustular rosacea (subtype 2).

Flushing is a congestive or vasomotor outbreak, a phenomenon which is expressed by the appearance of transient red spots mainly at the face and accompanied with a sensation of heat. This symptom is common to several pathologies including rosacea.

Flushing may be triggered by various stimuli of daily life: Fast change of temperature, food, alcoholic beverages.

Its unexpected and elusive nature makes it difficult to study.

Presently in clinical trials, the assessment of the efficiency of candidate drugs is carried out via a questionnaire given to the patient who records in his/her daily life, the occurrence of this symptom and attempts to characterize it.

Certain methods have been proposed for measuring flushing. For example, Wilkin (J Invest Dermatol, 1981, 76, 15-18) propose the use of a thermal circulation index. This index is the ratio of the effective heat conductivity of cutaneous tissues relatively to the effective heat conductivity of the environment. In order to measure flushing, this author proposes the measurement of malar skin and the measurement of the malar thermal circulation index. These parameters are measured before the stimulus and upon maximum change in the malar temperature. Next, the ratio between both of these measurements is studied. Moreover, the time between the application of the stimulus and the moment corresponding to half of the maximum change in malar temperature was measured. However, these methods do not give the possibility of differentiating a pathological flush (notably of a subject suffering from rosacea) from a normal flush (healthy subject).

Thus, there still exists a great need for a stricter and reproducible method for measuring congestive outbreaks, notably those related to rosacea, and to thereby assess the impact of candidate drugs on this symptom. Notably, there exists a need for a method not coming under or not uniquely from the appreciation of the patient and giving the possibility of obtaining statistically significant results with a group of patients as small as possible.

SUMMARY OF THE INVENTION

The inventors have developed a method for measuring flushes in a significant and reproducible way in a small number of subjects and giving the possibility of discriminating between flushes related to rosacea and those of subjects not affected by this disease. The results obtained by this method are perfectly correlated with those obtained by standard clinical assessment. This method may therefore be used during tests for assessing the efficiency of candidate drugs for rosacea, in particular during clinical trials. Further, the method has the advantage of not depending on self-assessment of the patient.

The present invention therefore relates to a method giving the possibility of measuring flushing in a subject comprising:
  a) subjecting the subject to a stimulus inducing flushing;
  b) measuring the blood inflow at the face of the subject for a period of time covering the flushing; and,
  c) calculating the entropy of the blood inflow.

Preferably, the measurement of the blood inflow at the face is achieved by measuring the intensity of the blood flow in surface skin portions of the face and/or measuring the color of the skin of the face, in particular the redness.

Preferably, the measurement of the intensity of the blood flow in the surface skin portions of the face is achieved by measuring the blood microcirculation, for example with a system based on the Doppler affect or with a system based on the analysis of the laser granularity contrast. In particular, the measurement of the intensity of the blood flow in the surface skin portions of the face is achieved by analyzing the laser granularity contrast, notably by means of a FLPI (full field laser perfusion imaging) imager.

In particular, the measurement of the blood inflow, preferably the intensity of the blood flow in the surface skin portions of the face, is achieved on a cheek or both cheeks. Preferably, the period of time during which the blood inflow is measured, preferably the intensity of the blood flow, is comprised between 30 min and 1 h 30 min, preferably between 45 min and 60 min.

Optionally, the method further comprises regular assessment of the heat sensation felt by the subject.

The stimulus inducing flushing may be selected from a hot drink, the absorption of a spice or an alcoholic beverage, preferably a hot drink or the absorption of a spice, still preferably a hot drink.

Preferably, the calculated entropy is indicative either of normal flush, or of pathological flush, in particular characteristic of rosacea. The calculated entropy may be compared with a range of reference entropy values, preferably with a range of entropy values characteristic of normal flush and/or with a range of entropy values characteristic of pathological flush, in particular characteristic of rosacea.

Preferably, the entropy is calculated with the following formula:

$$\text{Entropy} = -\Sigma(N(i)/Nt * \log(N(i)/Nt))$$

with N(i) is the number of points per interval of blood flow intensity;

Nt is the total number of points, i.e. $Nt = \Sigma N(i)$.

In a particular embodiment, several measurements of flushes are carried out for a subject. Notably, it is possible to make measurements on the left and right cheeks of the subject and the entropy is calculated either for each cheek or by averaging both cheeks.

In a particular embodiment, the measurement is made on a subject before and after treatment with a drug or drug candidate, a cosmetic product or a medical device, in particular intended for treatment of rosacea. In a first embodiment, the measurement is made on a subject on a cheek which has not received any treatment or has received a reference treatment or a placebo, and on the other cheek which has received a treatment with a drug or drug candidate, a cosmetic product or a medical device. In another embodiment, the measurement is made on a subject before and after treatment with a drug or drug candidate, a cosmetic product or a medical device. Preferably, the entropies calculated without any treatment or with a reference treatment or a placebo or with treatment with a drug or drug candidate, a cosmetic product or a medical device, are compared and allow determination of the therapeutic efficiency of said drug or drug candidate, cosmetic product or medical device. Preferably, the drug or drug candidate, cosmetic product or medical device is intended for treating rosacea. In a preferred embodiment, the subject is a subject suffering from rosacea.

Thus, the present invention relates to the use of the method for measuring flushing in a subject in order to determine the efficiency of a drug or drug candidate, of a cosmetic product or of a medical device, notably having the purpose of decreasing or suppressing pathological flushes, in particular those associated with rosacea. In particular, pathological flushes are associated with rosacea of subtype I, erythemotelangiectasic or of subtype II, papulopustular rosacea.

DETAILED DESCRIPTION OF THE INVENTION

The present invention relates to a method for measuring flushes. This method has the advantage of being capable of differentiating pathological flushes, notably those associated with rosacea, normal flushes, i.e. of subjects not having any pathology. This method gives a reproducible result and gives the possibility of carrying out statistically significant studies with a small number of subjects, notably about ten subjects. Thus, the present method is extremely useful for testing the efficiency of a treatment having the purpose of decreasing or suppressing pathological flushes, notably those associated with rosacea.

The present invention therefore relates to a method for measuring flushing in a subject comprising:
  a) subjecting the subject to a stimulus inducing flushing;
  b) measuring the blood inflow at the face of the subject during a period of time covering the flushing; and,
  c) calculating the entropy of the blood inflow.

The stimulus used may be selected from those well known to one skilled in the art. For example, this may be a hot drink, for example from 40-70° C., notably 60° C., the absorption of a spice, notably tabasco or a pepper, or an alcohol like wine. The hot drink may be water, coffee or tea. In a preferred embodiment, the stimulus is a hot drink or the absorption of a spice. In the preferential embodiment, the stimulus is a hot drink.

Optionally, before administering the stimulus, the subject will have been set up and left for a relaxation time, for example about 30 minutes.

Subsequently to the application of the stimulus, the blood inflow at the face of the subject is measured. The blood inflow is measured during a period covering the flushing. For example, it is measured from the moment of the stimulus up to the end of the flushing. This period preferably lasts from 30 minutes to 1 hour 30 minutes. In a preferred embodiment, it lasts for 45 to 60 minutes. In the preferred embodiment, it lasts for about 45 minutes. The measurement period may also comprise a period before applying the stimulus. This gives the possibility of defining a base level.

The blood inflow is measured during the whole selected period. Preferably, it is measured every minute, preferably every 10 to 50 seconds, still preferably at a frequency of at least every 10 seconds, for example at least or about every 5, 2 seconds or 1 second.

The blood inflow may be measured in different ways.

For example, the blood inflow at the face may be measured by the intensity of the blood flow in the surface skin portions of the face, by measuring the color of the skin of the face, in particular the redness, by regular assessment of the heat sensation felt by the subject, or by a combination of two or three of these parameters.

Thus, in a first embodiment, the blood inflow at the face is measured by measuring the intensity of the blood flow in surface skin portions of the face. Further, this measurement may be combined with the measurement of the color of the skin of the face, in particular the redness, and/or regular assessment of the heat sensation felt by the subject. Preferably, this measurement may be combined with the measurement of the color of the skin of the face, in particular the redness.

In a second embodiment, the blood inflow at the face is measured by measuring the color of the skin of the face, in particular the redness. Further, this measurement may be combined with measurement of the intensity of the blood flow in the surface skin portions of the face and/or regular assessment of the heat sensation felt by the subject. Preferably, this measurement may be combined with the measurement of the intensity of the blood flow in the surface skin portions of the face.

The blood inflow may be measured in the surface skin portions of the face corresponding to the forehead, to the chin and/or to the cheeks. In a preferred embodiment, it is measured at the cheeks. In a preferred embodiment, the blood inflow is measured for each of the cheeks.

When the method comprises the measurement of the intensity of the blood flow in the surface skin portions of the face, this measurement is conducted by measuring blood microcirculation, for example with a system based on the Doppler effect or with a system based on the analysis of the laser granularity contrast. In particular, the measurement of the intensity of the blood flow in the surface skin portions of the face is conducted by analyzing the laser granularity contrast, notably by means of an FLPI (full field laser perfusion imaging) imager. In a preferred embodiment, the skin microcirculation is measured with an FLPI (full field laser perfusion imaging) imager. For example, it is possible to use the apparatus marketed by Moor.

When the method comprises the measurement of the color of the skin of the face, in particular the redness, the measurement of redness may be conducted with any system giving the possibility of measuring color, preferably without any contact, for example a spectroradiometer, spectral/multispectral imaging, digital, still camera, or camera.

When the method comprises regular assessment of the heat sensation felt by the patient, this assessment will be made by the subject every 5 to 10 minutes. Notably, the latter may be made by determining a scale of scores. For example, such a scale may be the following: 1 for no heat sensation; 2 for a very slight heat sensation; 3 for slight heat sensation; 4 for moderate heat sensation; 5 for strong heat sensation.

On the basis of the measurement of the blood flow versus time, it is then possible to calculate the entropy of the intensity of the blood flow.

Indeed, the inventors noted that, surprisingly, healthy subjects also had a flush subsequent to the application of a stimulus. It was therefore important to distinguish flushing associated with a pathology such as rosacea, most particularly rosacea of subtype I, from flushing of a healthy subject. The inventors noticed that it was difficult to define an analysis factor allowing discrimination of both groups. Indeed, the maximum intensity was not discriminating. Although the duration of the flushes of subjects suffering from rosacea seems to be longer, this criterion was not sufficient for discriminating both groups, in particular when the number of subjects studied is restricted. The area under the curve of the blood flow intensity curve versus time may optionally be used but this criterion requires significant numbers of subjects in order to be able to be used.

Therefore it is quite surprising that the inventors identified entropy as a criterion capable of discriminating between both groups, this in a reproducible way and on very reduced numbers of subjects. Indeed, about ten subjects are sufficient.

In order to calculate this entropy, one skilled in the art may use all well known methods for assessing or calculating the entropy of a signal.

Notably, any method giving the possibility of estimating whether the subject spends more time in high blood inflow values.

In a preferred embodiment, the entropy of the blood flow intensity may be calculated by Shannon's entropy. Thus, this entropy may be calculated with the following formula:

$$\text{Entropy} = -\Sigma(N(i)/Nt * \log(N(i)/Nt))$$

with $N(i)$ is the number of points per interval of blood flow intensity;

$Nt$ is the total number of points, i.e. $Nt = \Sigma N(i)$.

The interval of blood flow intensity is defined by one skilled in the art according to the accuracy which he/she wishes to have.

For example, by considering the range covered by the minimum and maximum intensities of blood flows, it is possible to decide to subdivide this range into a certain number of intervals. Notably, the number of intervals may be comprised between 20 and 500, preferably between 50 and 250.

Alternatively, it may be decided to define the intervals with a blood flow intensity interval. For example, the intervals may be from 20 to 250, preferably from 10 to 50.

Thus, an entropy is obtained. The calculated entropy may then be compared with reference values. The reference entropy values may be those characteristic of pathological flushes, in particular associated with rosacea, and/or those characteristic of normal flushes. On the basis of this comparison, it may be determined whether the entropy corresponds to a normal flush, i.e. in a healthy subject, or to a pathological flush, notably characteristic of a subject suffering from rosacea.

In another preferred embodiment, the blood flow intensity data versus time may be transformed into a diagram following the principle explained in FIG. 5. Thus, blood flow intensity intervals are defined. For example, they may be defined as detailed above. Next, the number of points per blood flow intensity interval is determined. It corresponds to the Ni defined above. Finally, the diagram illustrating the number of points versus intensity intervals is prepared. On the basis of this diagram, it is possible to distinguish pathological flushes, in particular associated with rosacea, from those which are normal (FIGS. 6 and 7). Indeed, in this illustrative form, the inventors observed that normal flushes are characterized by a narrow peak while pathological flushes are characterized by a spread average intensity curve.

In an embodiment, several measurements of flushing are conducted for a subject according to the present method. For example, for a same subject, measurements on left and right cheeks of the subject may be made and the entropy is calculated either for each cheek, or by averaging both cheeks.

The present invention relates to the use of the method giving the possibility of measuring flushing in a subject according to present invention for determining the efficiency of a drug or drug candidate, of a cosmetic product or of a medical device, notably having the purpose of decreasing or suppressing pathological flushes, in particular those associated with rosacea, preferably rosacea of subtype I, or rosacea of subtype II or for providing useful information for determining the efficiency of a drug or drug candidate, of a cosmetic product or of a medical device.

Thus, the present invention relates to a method allowing determination of the efficiency of a drug or drug candidate, a cosmetic product or a medical device, notably having the purpose of decreasing or suppressing pathological flushes, or of generating useful information for determining the efficiency of a drug or drug candidate, a cosmetic product or a medical device, in which several measurements of flushes are conducted. By "measurement of flushes" is meant the steps for applying the stimulus and measuring the blood flow. Indeed, the entropy may be directly calculated following both of these steps or subsequently during analysis of the results.

Notably, several measurements of flushes are carried out on the same subject at several moments. Preferably, one measurement is conducted before initiating the treatment with the drug or drug candidate, the cosmetic product or the medical device. Next, a measurement is conducted at the end of the treatment with the drug or drug candidate, cosmetic product or medical device. Finally, several intermediate measurements may be conducted during the treatment with the drug or drug candidate, the cosmetic product or the medical device. The entropies may be calculated on the totality of the acquired signal or on a portion of the signal, notably on the signal acquired before the stimulus and on the signal acquired after the stimulus. The calculated entropies after or during the treatment are compared with the entropy calculated before initiating the treatment. If the calculated entropy after or during the treatment is less than the calculated entropy before initiating the treatment, the drug or drug candidate, cosmetic product or medical device, may be considered as efficient, notably efficient for decreasing or suppressing pathological flushes. Notably, it is also possible to compare the calculated entropy after or during the treatment with reference entropy values and to determine whether the calculated entropy corresponds to a normal flush, i.e. in a healthy subject, or to a pathological flush, notably characteristic of a subject suffering from rosacea. Preferably, this method is applied on a group of subjects, for example a group comprising at least 10, 15 or 20 subjects, notably a group from 10 to 100 subjects.

This method may also comprise control groups. Control groups may be subjects suffering from the pathology and which are treated with a reference drug, such as a drug recognized for its efficiency, notably efficient for reducing or suppressing pathological flushes. The control groups may also be subjects suffering from the pathology and which are treated with a placebo or which have not received any treatment.

Alternatively, using the subject as a control may be contemplated. Thus, for example, the subject has been treated for one half of his/her face with the drug or drug candidate, the cosmetic product or the medical device, while the other half of the face was treated with a reference drug, a placebo or did not receive any treatment. Most particularly, the relevant parts of the face are the cheeks. In this context, a measurement of flushes is made on each cheek and the entropy is calculated for each of the cheeks. Like in the previous embodiment, a measurement of flushes is preferably made before initiating the treatment with the drug or drug candidate, the cosmetic product or the medical device, and also at the end of the treatment, and optionally during treatment. Thus, in addition to the data corresponding to the time-dependent change in the entropy according to the treatment, it is also possible to compare on a same subject the entropy calculated for one cheek with that calculated for the other cheek.

Preferably, the drug or drug candidate is intended for treating rosacea, of subtype I, or erythemotelangiectasic rosacea and of subtype II or papulopustular rosacea and more particularly erythemotelangiectasic rosacea of subtype I. In a preferred embodiment, the subject is a subject suffering from rosacea, in particular from erythemotelangiectasic rosacea of subtype I.

The following examples will now be given, as an illustration and without any limitation.

DESCRIPTION OF THE FIGURES

FIG. 6: Averaged histogram illustrating the number of points versus intensity intervals (100 intervals) of the signal for one cheek (number of subjects=12 subjects suffering from rosacea (dotted line) and 13 healthy subjects (solid line)).

FIG. 7: Standardized histogram for healthy subjects (FIG. 7A) and for subjects suffering from rosacea (FIG. 7B) by using the signals after the stimulus.

FIG. 8: Histogram illustrating the average entropy as measured on the cheeks for 3 consecutive days for 10 subjects (250 intervals) (on the left, right cheek (2); on the right, left cheek (3)).

EXAMPLES

Figure 1:
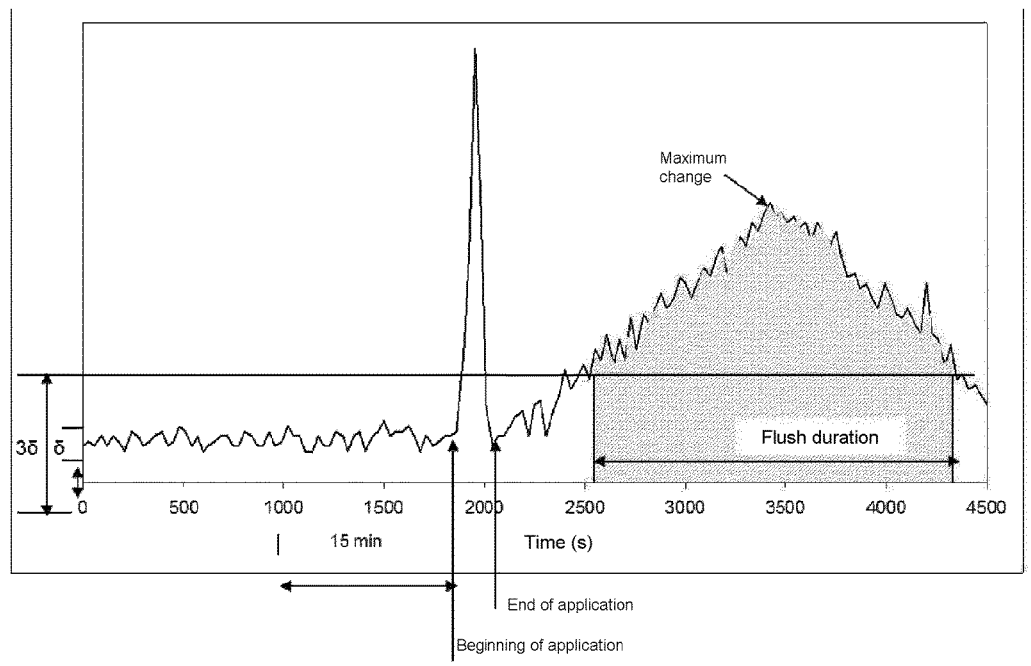
FIG. 1: Schematic description of the flush phenomenon illustrating a curve of the intensity of the signal, recorded versus time, upon measuring the blood flow in the surface skin portions of a cheek.
Figure 5:
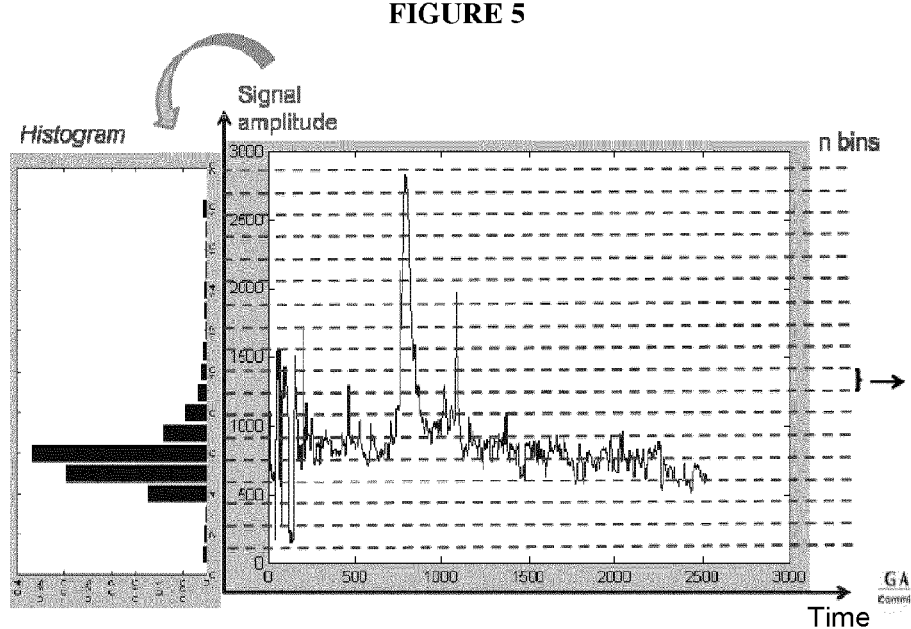
FIG. 5: Explanatory diagram on the method giving the possibility of preparing the histogram illustrating the number of points versus intensity intervals of the signal from a curve of the intensity of the recorded signal versus time during measurement of the circulatory flow.

Methodology
Patients:
15 patients suffering from rosacea of sub-type I
15 healthy subjects.
The stimulus, administered orally, was:
Water at 60° C., 200 ml; or
Tabasco (6 drops)
Procedure:
Installation of the subject and rest for 30 minutes.
Measurements after stimulus for 45 minutes comprising:
Measurement of blood flow in the surface skin portions (FLPI=full field laser perfusion imaging) of the face. For the face, the measurement was made at each cheek. The skin microcirculation was measured with an FLPI imager from Moor by using analysis of the laser granularity contrast (LASCA).
The intensity of the blood flow versus time is obtained (see curve of FIG. 1 for an illustration).
Analysis of the results:
Several parameters were taken into account for analyzing the results. Indeed, on the basis of the obtained curves (see FIG. 1 for an illustration), the following parameters were measured:
The maximum intensity during flushing;
duration of the flushing; and
the area under the curve (AUC).
Analysis of the results by entropy:
On the basis of the intensity of the blood flow versus time, this curve was processed in the following way (for an illustration, see FIG. 5). The number of points per intensity interval of the blood flow was determined, and a histogram is then plotted illustrating the number of points N(i) according to the intensity intervals. The intensity interval which was used for generating the results is number 20.
More specifically, the entropy of the signal calculated by means of the histogram, may be calculated by the following formula (Shannon's entropy):

Entropy=$-\Sigma(N(i)/Nt^*\log(N(i)/Nt))$ with N(i) the number of points per intensity interval
Nt the total number of points, i.e. Nt=$\Sigma$N(i).
The histograms of the signal may be prepared separately per subject (exemplary histogram in FIG. 5). Alternatively, in order to minimize the inter-individual variabilities, the histograms may also be prepared by using data obtained for several subjects of the same category, either healthy, or suffering from rosacea.
In the same way, the entropies may be calculated for each subject with the formula indicated above. Next, the calculated entropies may be used for calculating averages of the entropies for several subjects of a same category, either healthy or suffering from rosacea.

Figure 2:
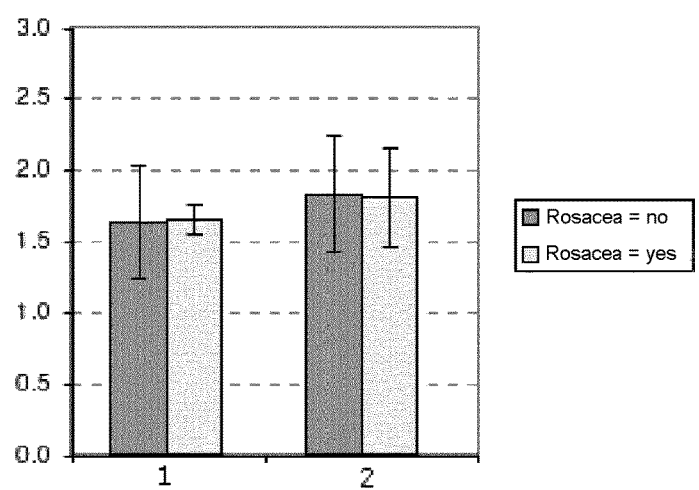
FIG. 2: Histogram illustrating the maximum change factor of the intensity relatively to the basal level in healthy subjects and in subjects suffering from rosacea.
Figure 3:
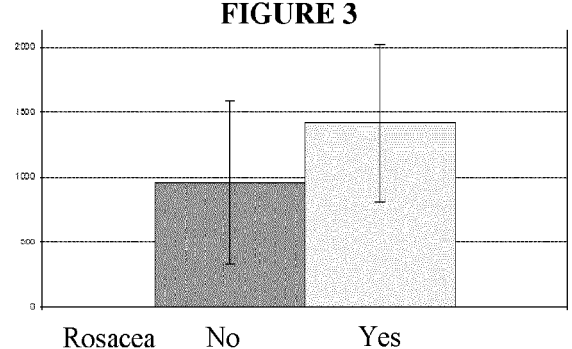
FIG. 3: Histogram illustrating the duration of flushing in healthy subjects and in subjects suffering from rosacea.
Figure 4:
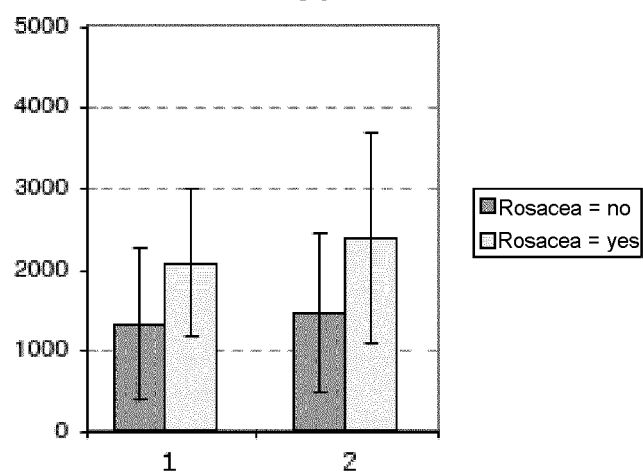
FIG. 4: Histogram illustrating the area under the curve (AUC) in healthy subjects and in subjects suffering from rosacea.
Figure 9:
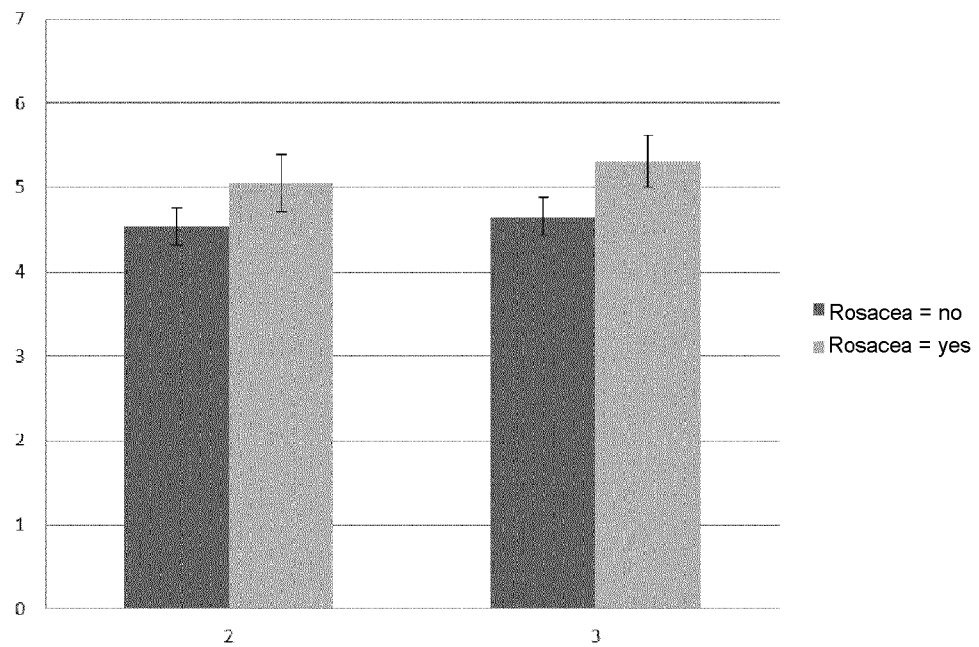
FIG. 9: Histogram illustrating the average entropy as measured on the cheeks after the hot water stimulus for 12 subjects suffering from rosacea and 13 healthy subjects (250 intervals) (on the left, right cheek (2); on the right, left cheek (3)).
Figure 10:
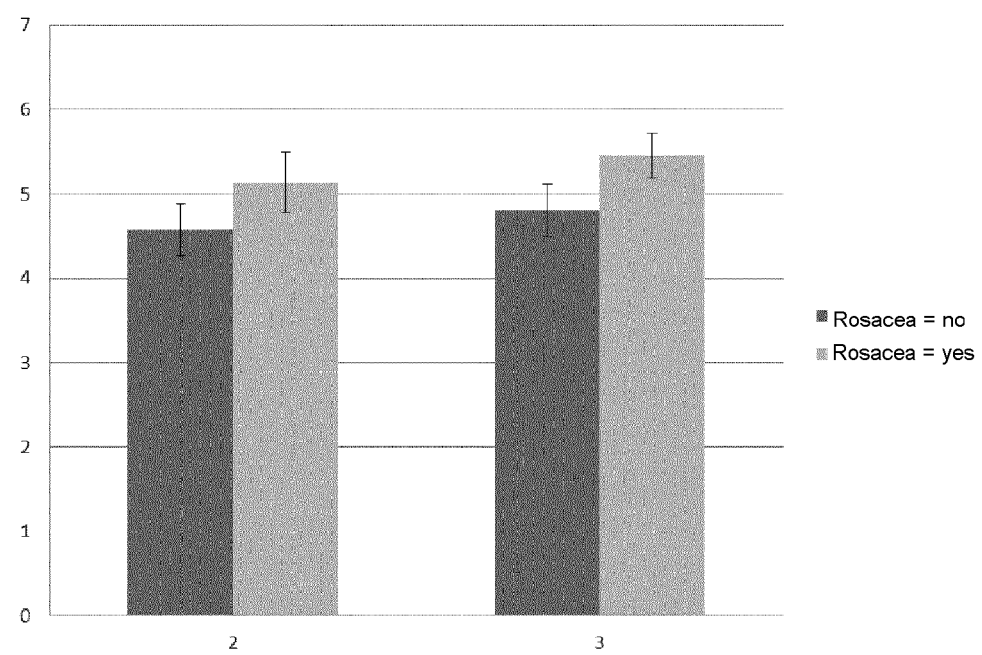
FIG. 10: Histogram illustrating the average entropy as measured on the cheeks after the tabasco stimulus for 12 subjects suffering from rosacea and 13 healthy subjects (250 intervals) (on the left, right cheek (2); on the right, left cheek (3)).
Figures 11, 12:
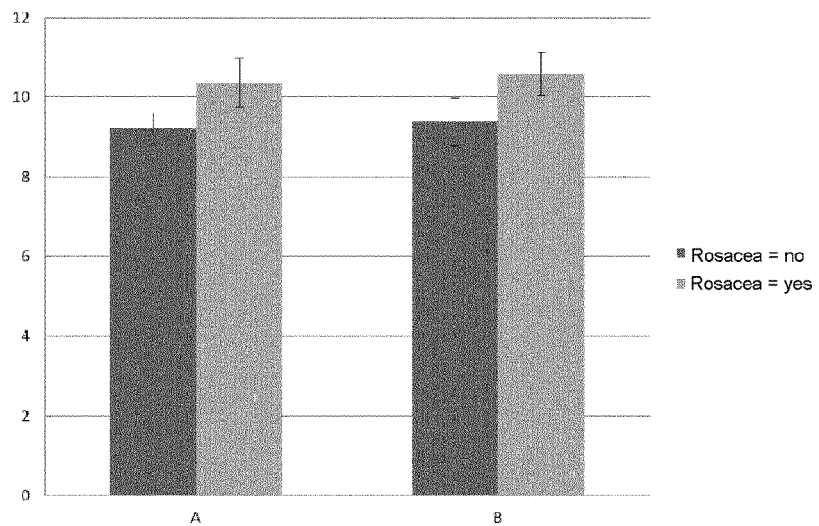
FIG. 11: Histogram illustrating the sum of the entropies as measured on both cheeks after the hot water stimulus (A) or tabasco stimulus (B) for 12 subjects suffering from rosacea and 13 healthy subjects (250 intervals) (on the left, right cheek; on the right, left cheek).
FIG. 12: A table illustrating, according to the stimulus used and the measured parameter, the number of subjects required for differentiating the flushing of healthy subjects from the flushing of subjects suffering from rosacea.

The entropies may be calculated on the totality of the acquired signal or on a portion of the signal, notably on the signal acquired before the stimulus and on the signal acquired after the stimulus.
Results
The first parameters which were taken into account for analyzing the results were the maximum intensity during flushing, its duration and the area under the curve.
On the basis of these parameters and with the relevant number of subjects, it was determined by the inventors that it was not possible to statistically significantly distinguish the flushes of healthy subjects from those of subjects suffering from rosacea: see FIG. 2 for the maximum intensity; FIG. 3 for the duration of the flush; and FIG. 4 for the area under the curve.
The inventors therefore sought another method for analyzing blood flow data so as to be capable of distinguishing the response of healthy subjects from that of subjects suffering from rosacea. For this, they built histograms of the signal (see FIG. 5) which allow the calculation of the entropy of the signal.
Histograms of the signals gave the possibility of obtaining curves which clearly differ between healthy subjects and subjects suffering from rosacea (FIGS. 6 and 7). Indeed, in healthy subjects, a very large number of points is present for the intervals of low signal intensities, while, in subjects suffering from rosacea, a moderately large number of points having great signal intensity variability is observed.
On the basis of these data, an entropy was calculated as indicated above (Shannon's entropy). As shown in FIGS. 9-11, statistically different entropies were obtained for both groups of subjects.
The measurement of the flushes was made for three consecutive days on 10 subjects. As shown in FIG. 8, this measurement is reproducible over three consecutive days.
FIGS. 9-11 demonstrate that the calculated entropy gives the possibility of statistically significantly distinguishing the flushes of healthy subjects from those of subjects suffering from rosacea.
Under the experimental and analysis conditions used with FLPI, by considering an interval of intensity 20 for the calculation of the histograms, it is observed that the healthy subjects have an entropy value around 4.5, while the subjects suffering from rosacea have an entropy value around 5.2.
Finally, the table of FIG. 12 shows that the method for measuring flushes developed by the inventors is highly advantageous since a cohort of about 10 subjects is sufficient. On the contrary, if the criteria of the area under the curve was used, a minimum of at least 55 subjects would be needed.

The invention claimed is:
1. A method for measuring a flush in a subject, the method comprising:
a) subjecting the subject to a stimulus inducing a flush;
b) measuring blood inflow intensity at a surface skin area of the subject's face for a period of time covering the flushing;
c) analyzing the blood flow intensity using a system based on laser granularity contrast;
d) calculating entropy of the blood inflow using the following formula:

$$\text{Entropy} = -\Sigma \left( \frac{N_{(i)}}{N_t} \times \log\left(\frac{N_{(i)}}{N_t}\right) \right)$$

wherein $N_{(i)}$ is the number of points per intensity interval of the blood flow, and wherein $N_t$ is the total number of points, such that $N_t = \Sigma N_{(i)}$, and (e) using the calculated entropy to determine the therapeutic efficiency of a drug or drug candidate, a cosmetic product or a medical device.

2. The method according to claim 1, wherein the system based on laser granularity contrast is a full field laser perfusion imaging (FLPI) imager.

3. The method according to claim 1, wherein the measurement of the blood flow intensity in the surface skin portions of the subject's face is made by measuring blood microcirculation.

4. The method according to claim 1, wherein the measurement of the blood inflow is made on one or both cheeks of the subject's face.

5. The method according to claim 1, wherein the period of time during which the blood inflow is measured, is from 30 min to 1 hour and 30 minutes.

6. The method according to claim 5, wherein the period of time during which the blood inflow is measured, is from 45 minutes to 60 minutes.

7. The method according to claim 5, wherein the stimulus is a hot drink or absorption of a spice.

8. The method according to claim 7, wherein the stimulus is a hot drink.

9. The method according to claim 1, wherein the method further comprises regular evaluation of a heat sensation felt by the subject.

10. The method according to claim 1, wherein the stimulus inducing the flush is a hot drink, absorption of a spice, or an alcoholic beverage.

11. The method according claim 1, wherein the calculated entropy is indicative either of normal flush, or pathological flush.

12. The method according to claim 1, wherein the calculated entropy is compared with a range of reference entropy values.

13. The method according to claim 12, wherein the calculated entropy values are compared with a range of characteristic entropy values of a normal flush and/or with a range of entropy values characteristic of a pathological flush.

14. The method according to claim 1, wherein several measurements of flushes are carried out for one subject.

15. The method according to claim 14, wherein measurements are carried out on the left and right cheeks of the subject's face and the entropy is calculated either for each cheek or by averaging the measurement of both cheeks.

16. The method according to claim 14, wherein the measurement is carried out on a subject before and after treatment with the drug or drug candidate, the cosmetic product or the medical device.

17. The method according to claim 16, wherein entropies calculated without any treatment or with treatment with a reference treatment or a placebo and with a treatment by the drug or drug candidate, the cosmetic product or the medical device, are compared and allow determination of the therapeutic efficiency of said drug or drug candidate, cosmetic product or medical device.

18. The method according to claim 16, wherein the drug or drug candidate is intended for treating rosacea.

19. The method according to claim 14, wherein the measurement is carried out on a subject on one cheek which has not received any treatment or has received a reference treatment or a placebo, and on the other cheek that has received a treatment with the drug or drug candidate, the cosmetic product or the medical device.

20. A method of determining the efficacy of a drug or drug candidate, of a cosmetic product or of a medical device, the method comprising:

performing a method for measuring flush in a subject, the method comprising:

a) subjecting the subject to a stimulus inducing a flush;

b) measuring blood inflow intensity at a surface skin area of the subject's face for a period of time covering the flushing;

c) analyzing the blood flow intensity using a system based on laser granularity contrast; and d) calculating entropy of the blood inflow using the following formula:

$$\text{Entropy} = -\Sigma \left( \frac{N_{(i)}}{N_t} \times \log\left(\frac{N_{(i)}}{N_t}\right) \right)$$

wherein $N_{(i)}$ is the number of points per intensity interval of the blood flow, and wherein $N_t$ is the total number of points, such that $N_t = \Sigma N_{(i)}$, and conducting the method for measuring flush to determine if the drug, drug candidate, cosmetic product or medical device is effective in reducing or suppressing pathological flushes.

21. The method according to claim 20, wherein the pathological flushes are associated with rosacea.

22. The method according to claim 21, wherein the pathological flushes are associated with erythemotelangiectasic rosacea of subtype I.

23. The method according to claim 21, wherein the pathological flushes are associated with papulopustular rosacea of subtype II.

* * * * *